(12) United States Patent
Doering

(10) Patent No.: US 9,804,137 B2
(45) Date of Patent: Oct. 31, 2017

(54) METHOD AND DEVICE FOR CALIBRATING AN EXHAUST GAS SENSOR

(71) Applicant: MAN Truck & Bus AG, Munich (DE)

(72) Inventor: Andreas Doering, Munich (DE)

(73) Assignee: MAN TRUCK & BUS AG, Munich (DE)

( * ) Notice: Subject to any disclaimer, the term of this patent is extended or adjusted under 35 U.S.C. 154(b) by 370 days.

(21) Appl. No.: 14/713,507

(22) Filed: May 15, 2015

(65) Prior Publication Data
US 2015/0276696 A1    Oct. 1, 2015

Related U.S. Application Data

(62) Division of application No. 14/075,481, filed on Nov. 8, 2013, now abandoned.

(30) Foreign Application Priority Data

Nov. 9, 2012    (DE) .................. 10 2012 021 928

(51) Int. Cl.
*G01N 33/00*    (2006.01)
*G01N 27/417*    (2006.01)

(52) U.S. Cl.
CPC ..... *G01N 33/0006* (2013.01); *G01N 27/4175* (2013.01)

(58) Field of Classification Search
CPC .................................. G01N 33/0006
See application file for complete search history.

(56) References Cited

U.S. PATENT DOCUMENTS

| | | |
|---|---|---|
| 3,593,023 A | 7/1971 | Dodson |
| 4,578,986 A | 4/1986 | Navarre |
| 4,856,352 A | 8/1989 | Daum |
| 6,242,263 B1 | 6/2001 | Faber |
| 7,028,465 B2 | 4/2006 | Ripper |
| 7,696,501 B2 | 4/2010 | Jones |
| 7,975,524 B2* | 7/2011 | Sakai ................ G01N 27/4175 73/1.06 |
| 2012/0266646 A1 | 10/2012 | Maeda |
| 2013/0133400 A1 | 5/2013 | Jaeger |

FOREIGN PATENT DOCUMENTS

| | | |
|---|---|---|
| DE | 101 00 420 A1 | 7/2002 |
| DE | 10 2008 046 121 A1 | 3/2010 |

* cited by examiner

*Primary Examiner* — Robert R Raevis
(74) *Attorney, Agent, or Firm* — Lucas & Mercanti, LLP

(57) ABSTRACT

A method for calibrating an exhaust gas sensor arranged in a measurement chamber, includes providing a measurement chamber in or adjacent to an exhaust channel of an internal combustion engine. At the start of a calibration phase, exhaust gas present in the measurement chamber is displaced by a filling of the measurement chamber with calibration gas, and at the end of the calibration phase, exhaust gas diffuses into and/or is introduced into the measurement chamber.

16 Claims, 3 Drawing Sheets

METHOD AND DEVICE FOR CALIBRATING AN EXHAUST GAS SENSOR

CROSS-REFERENCE TO RELATED APPLICATIONS

This application is a divisional of U.S. patent application Ser. No. 14/075,481 (now abandoned), filed on Nov. 8, 2013, which claims the priority of DE 10 2012 021 928.8 filed Nov. 9, 2012, both of which are incorporated by reference herein.

BACKGROUND OF THE INVENTION

The invention concerns a method for calibrating an exhaust gas sensor and a device for calibrating an exhaust gas sensor.

To control the operation of internal combustion engines, exhaust gas sensors are used which supply measurement signals to the engine control system and/or to an exhaust gas aftertreatment system. The exhaust gas sensors used are primarily lambda sensors and $NO_x$ sensors. To be able to perform an effective catalytic reduction, for example by the controlled addition of urea, it is necessary to determine the $NO_x$ emissions in the exhaust gas flow from an internal combustion engine using $NO_x$ sensors. DE 101 00 420 A1 describes a method for controlling an exhaust gas aftertreatment system in which a predefinable quantity of reducing agent is supplied to the exhaust gas flow depending on the state of the internal combustion engine and/or the exhaust gas aftertreatment system.

To measure the oxygen content in the exhaust gas flow from an internal combustion engine, lambda sensors are used which are inserted as exhaust gas sensors in the exhaust system before and/or after a catalytic converter.

The exhaust gas sensors used are subject to an ageing process which means that during a lengthy operating period of an exhaust gas sensor, the measurement curve changes as a function of the operating period. To undertake calibration of a lambda sensor, in vehicle engines it is known in principle to calibrate the lambda sensor in overrun mode in which no exhaust gas is generated and the lambda sensor is exposed to the aspirated ambient air. Provided that the aspirated ambient air has an oxygen content of 20.942%, a measurement value output by the lambda sensor can be corrected accordingly if, because of a lengthy operating period, the lambda sensor is supplying a measurement value deviating from the actual value. Such a measurement value adaptation can be carried out for example by applying a correction factor to the measurement value output by the lambda sensor.

DE 10 2008 046 121 A1 discloses a method for calibrating an exhaust gas sensor which is arranged in an exhaust pipe of an internal combustion engine and protrudes laterally into an exhaust channel. To calibrate the exhaust gas sensor, its measurement tip is exposed to a passing flow of flushing air. This document also mentions the possibility that a screening device can be guided at the measurement tip in order to conduct the flushing air to the measurement tip in a targeted fashion. In normal operating mode, the screening device is removed from the exhaust pipe.

SUMMARY OF THE INVENTION

The invention is based on the object of specifying a method for calibrating an exhaust gas sensor which allows calibration to be performed as quickly and precisely as possible.

According to an embodiment of the invention, it is proposed that at the start of the calibration phase, the exhaust gas present in a measurement chamber in which the exhaust gas sensor is located is displaced by a filling of the measurement chamber with calibration gas, and that after the end of the calibration phase, exhaust gas is diffused and/or introduced into the measurement chamber. By a deliberate introduction of calibration gas with the corresponding pressure, the exhaust gas present in the measurement chamber before the calibration phase is quickly expelled therefrom. Preferably then, during the calibration phase, at least a small quantity of calibration gas is still conducted into the measurement chamber, in order to ensure that no exhaust gas can penetrate the measurement chamber. After the end of the calibration phase, exhaust gas is again introduced directly into the measurement chamber, whereby the calibration gas therein escapes from the measurement chamber and normal measurement operation can be resumed very quickly. In principle here any suitable gas can be used as calibration gas. An embodiment variant is particularly preferred in which, in connection with charged internal combustion engines, compressed fresh air from at least one compressor is used as calibration gas.

During the calibration phase it can be sufficient if the measurement chamber is not completely screened or isolated from the exhaust gas flow, as would be the case for example if valves were used, if a constant supply of calibration gas to the measurement chamber ensures that no exhaust gas can penetrate the measurement chamber. An incomplete screening of the exhaust gas flow can be achieved for example if the measurement chamber is screened from the exhaust gas flow via a gas-permeable membrane, or if the calibration gas quantity supplied to the measurement chamber and/or the pressure predominating in the measurement chamber are so great that no exhaust gas can penetrate the measurement chamber.

A particularly advantageous embodiment provides that after the end of the calibration phase, exhaust gas is drawn and/or pressed into the measurement chamber in order to flush the measurement chamber rapidly. For this, after the end of the calibration phase, exhaust gas can be drawn into the measurement chamber by means of a suction device. Alternatively or also additionally, it can be provided that after the end of the calibration phase, the measurement chamber is connected fluidically to a part of the exhaust system in which a higher pressure predominates than in the measurement chamber, so that the exhaust gas is pressed into the measurement chamber.

The invention is also based on the object of creating a device for calibrating an exhaust gas sensor which allows a reliable calibration that can be performed as quickly as possible.

According to an embodiment of the invention, the exhaust gas sensor lies in a measurement chamber which is screened from the exhaust gas flow present in the exhaust channel by means of a screening device which is gas-permeable for at least part of the time. Calibration gas can be introduced into the measurement chamber via a gas pipe connected to the measurement chamber. By arranging the exhaust gas sensor in a measurement chamber which can be arranged in or directly adjacent to the exhaust channel, a controlled gas exchange in the measurement chamber can be achieved in order for example to be able to initiate the calibration phase very quickly. Calibration gas can then be fed into the measurement chamber via a gas pipe with corresponding pressure, causing a rapid displacement of the exhaust gas previously present in the measurement chamber. For the calibration gas to be able to be introduced into the measurement chamber, it is necessary for the screening device to be gas-permeable for at least part of the time.

A screening device which is gas-permeable for part of the time can consist of two perforated cylinders arranged concentrically one inside the other, of which at least one is movable about its longitudinal axis to change the screening effect. By rotation about its longitudinal axis, the perforations of the cylinder can be brought into an aligned position or into a non-aligned position. In an aligned position, the cylinder side walls are permeable to the exhaust gas flow so that this can flow through the measurement chamber. If however the cylinders are turned so that the perforations are not aligned, there is an at least largely sealed screening from the exhaust gas flow. The measurement chamber can then be filled with calibration gas in order to perform calibration of the exhaust gas sensor arranged in the measurement chamber.

The perforations in the cylinder walls can be formed as bores offset by 180°. This gives a measurement chamber which is formed by concentrically arranged cylinders and which has a relatively simple and reliable structure.

The measurement chamber can also be arranged directly adjacent to the exhaust channel of an internal combustion engine, wherein gas can be introduced into and extracted from the measurement chamber via a gas-permeable membrane which forms a screening device. Calibration gas can be introduced into the measurement chamber via a gas pipe connected to the measurement chamber, wherein exhaust gas present in the measurement chamber is then displaced into the exhaust channel through the gas-permeable membrane. During the calibration phase, a certain quantity of calibration gas can be introduced continuously into the measurement chamber to ensure that no exhaust gas penetrates the measurement chamber through the gas-permeable membrane. At the end of the calibration phase, the supply of calibration gas is stopped so that exhaust gas can again penetrate the measurement chamber via the gas-permeable membrane.

To achieve an accelerated penetration of exhaust gas into the measurement chamber, exhaust gas can also be drawn from the exhaust channel through the gas-permeable membrane via a suction line connected to the measurement chamber. The suction process can be carried out by means of a controllable suction device which for example can consist of a suction line—already present in any case—from an engine aspiration system, and a controllable valve in a suction line leading to the measurement chamber. Alternatively or in some cases also additionally, it can be provided that the measurement chamber is connected fluidically to a part of the exhaust system in which a higher pressure predominates than in the measurement chamber, so that the exhaust gas is pressed into the measurement chamber. Preferably here the exhaust gas is extracted upstream of an exhaust gas turbine of an exhaust turbocharger and/or upstream of a choke device and/or upstream of a silencer.

The invention is explained in more detail below with reference to exemplary embodiments shown in the drawings.

DETAILED DESCRIPTION OF THE PREFERRED EMBODIMENTS

Figure 1:
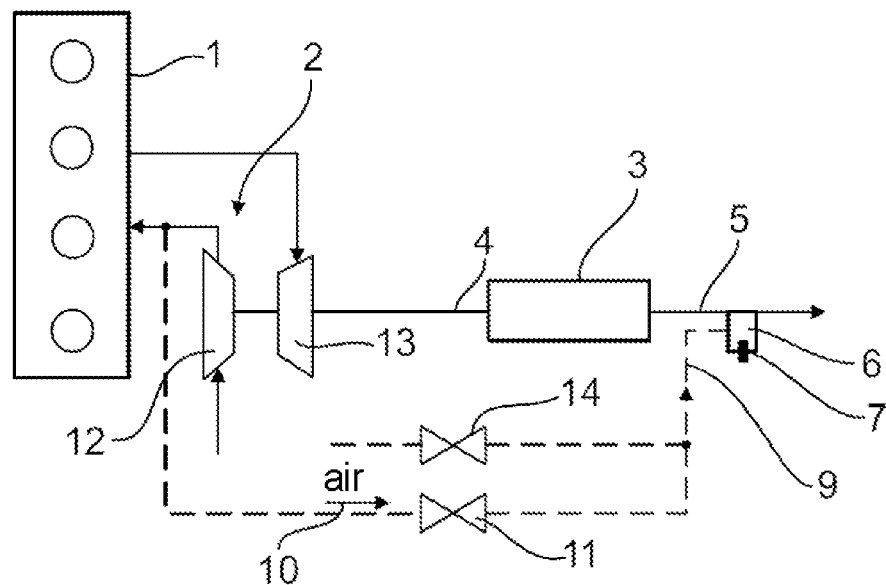
FIG. 1 is a schematic depiction of an internal combustion engine with an exhaust gas aftertreatment system, in which an exhaust gas sensor is connected to the exhaust channel.

FIG. 1 shows an internal combustion engine 1 with an exhaust turbocharger 2, to which an exhaust channel 4 is connected which leads to a catalytic converter 3. Downstream of the catalytic converter 3 is an exhaust channel 5, adjacent to which is a measurement chamber 6 with an exhaust gas sensor 7.

Figure 2:
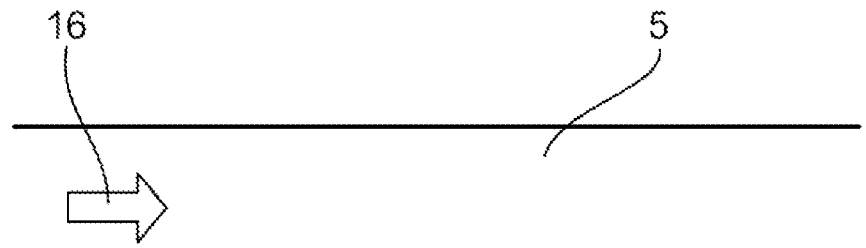
FIG. 2 is a schematic depiction of an arrangement of an exhaust gas sensor in a measurement chamber adjacent to an exhaust channel.
Figure 2:
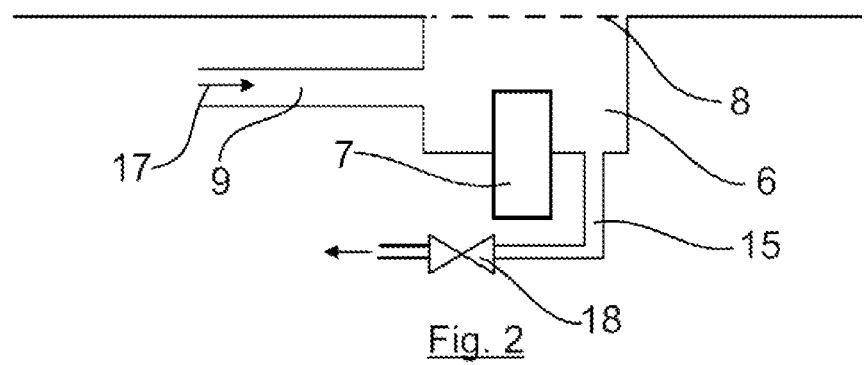

The measurement chamber 6, as shown in FIG. 2, is connected fluidically to the exhaust channel 5 via a gas-permeable membrane 8 (FIG. 2). To be able to introduce calibration gas into the measurement chamber 6, a gas pipe 9 is connected to the measurement chamber 6, via which for example air as a calibration gas can be fed according to the direction of arrow 10 via a controllable valve 11. On the output side the air is extracted from a compressor 12 belonging to the turbocharger 2, and enters the measurement chamber 6 when valve 11 is open. The compressor 12 here serves as the pressure generator and is part of the exhaust turbocharger 2 which is driven by exhaust gas from the internal combustion engine 1 via the turbine 13 of the turbocharger 2.

The calibration gas, for example air, supplied by the compressor to the measurement chamber 6 can be used to calibrate a lambda sensor where fitted, whereas in the case of other sensors such as for example NOx, NH3 or soot sensors, it can be used to determine the zero point.

In the embodiment example of FIG. 1, a further calibration gas with a predefined composition can be fed into the measurement chamber 6 via the gas pipe 9 via a second controllable valve 14. In this case the valve 11 is closed. The calibration gas for example has a predefined $NO_x$ concentration, whereby for example a correction factor can be determined for an exhaust gas sensor formed as an $NO_x$ sensor if the measurement value determined by the exhaust gas sensor deviates from the actual value of the $NO_x$ concentration supplied.

FIG. 2 shows in enlarged view the region where the measurement chamber 6 borders the exhaust channel 5. An exhaust gas sensor 7, connected electrically to a measurement system not shown in more detail, protrudes into the measurement chamber 6. Also the gas pipe 9 shown in FIG. 1 and a further suction line 15 are connected to the measurement chamber 6. The measurement chamber 6 is partly screened from the exhaust gas, which flows through the exhaust channel 5 in the arrow direction 16, by a gas-permeable membrane 8 forming a screening device.

If air or another calibration gas is fed into the measurement chamber 6 via gas pipe 9 according to the arrow direction 17, wherein the suction line 15 is blocked by a closed valve 18, this has the consequence that exhaust gas present is displaced from the measurement chamber 6 into the exhaust channel 5 through the membrane 8. Then only air or calibration gas is still present in the measurement chamber 6, so that a calibration measurement can be performed.

To end the calibration phase in the exemplary embodiment shown according to FIG. 2, exhaust gas is drawn into the measurement chamber 6 through the membrane 8 via suction line 15 when the valve 18 is open. The gas pipe 9 is now blocked. By drawing exhaust gas into the measurement chamber 6, the exhaust gas sensor 7 is quickly fully exposed to exhaust gas and the exhaust gas sensor can again be used for exhaust gas measurement in normal measurement operation.

Figure 6:
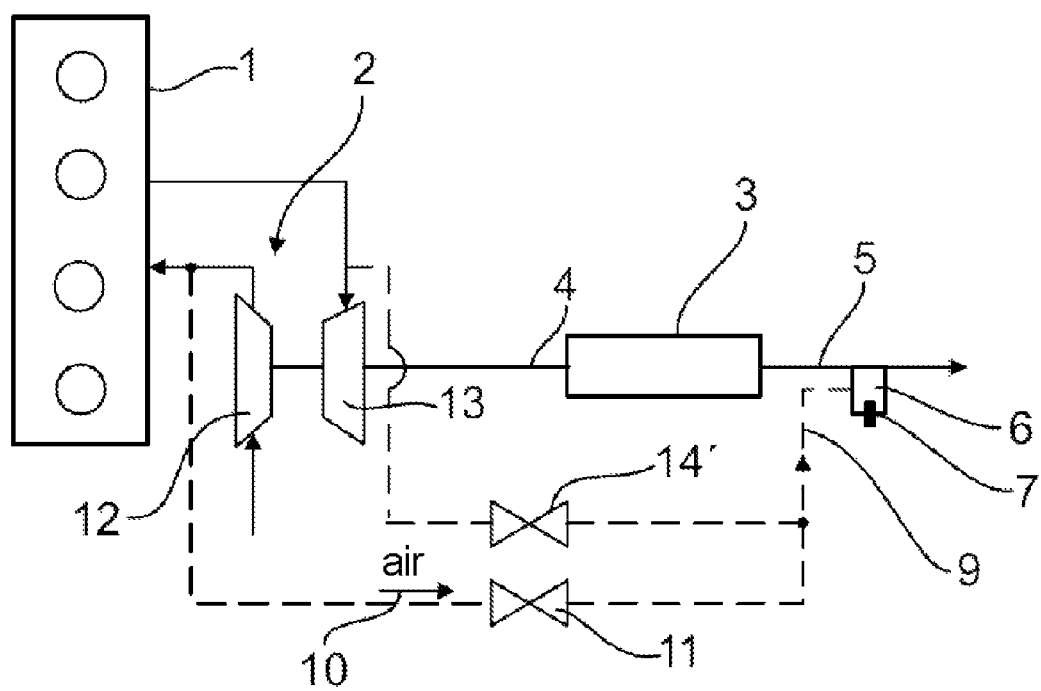
FIG. 6 is a schematic depiction of an alternative variant of the embodiment shown in FIG. 1 with which, after the end of the calibration phase, exhaust gas can be pressed into the measurement chamber.

The embodiment according to FIG. 6 shows an alternative, or in some cases also an additional, possibility to the embodiment in FIG. 1 for filling the measurement chamber with exhaust gas, wherein after the end of the calibration phase the exhaust gas is pressed into the measurement chamber. For this it is advantageous to extract exhaust gas at a point at which a higher exhaust gas back pressure predominates, so that the exhaust gas is pressed into the measurement chamber because of the pressure difference. In the case of internal combustion engines 1 with exhaust gas charging, it is therefore suitable to extract the exhaust gas upstream of the exhaust turbine 13, since here a significantly higher pressure predominates than downstream of the exhaust turbine 13. The extraction is preferably controlled or regulated by means of a controllable valve 14'. However extraction upstream of a choke point or fittings which raise the back pressure, such as a silencer, a catalytic converter or a choke flap, is in principle possible and conceivable.

The duration and frequency of the calibration phases can be set or modified depending on the operating state of the internal combustion engine and/or the exhaust gas aftertreatment system.

Figure 3:
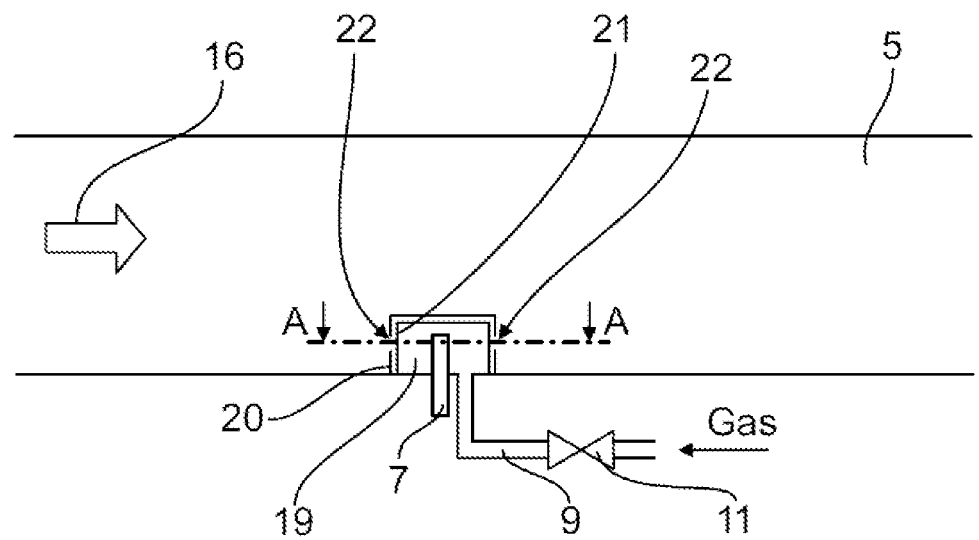
FIG. 3 is a schematic depiction of a measurement chamber which is formed in an exhaust channel and has an exhaust gas sensor.

FIG. 3 shows a preferred embodiment of a measurement chamber 19 which is arranged in an exhaust channel 5 and formed by two perforated cylinders 20, 21 arranged concentrically one inside the other. The exhaust gas sensor 7 protrudes into the measurement chamber 19. A gas pipe 9 is connected to the measurement chamber 19, via which air or flushing gas or calibration gas can be conducted into the measurement chamber 19. The gas pipe 9 can be closed by means of a controllable valve 11.

Figures 4, 5:
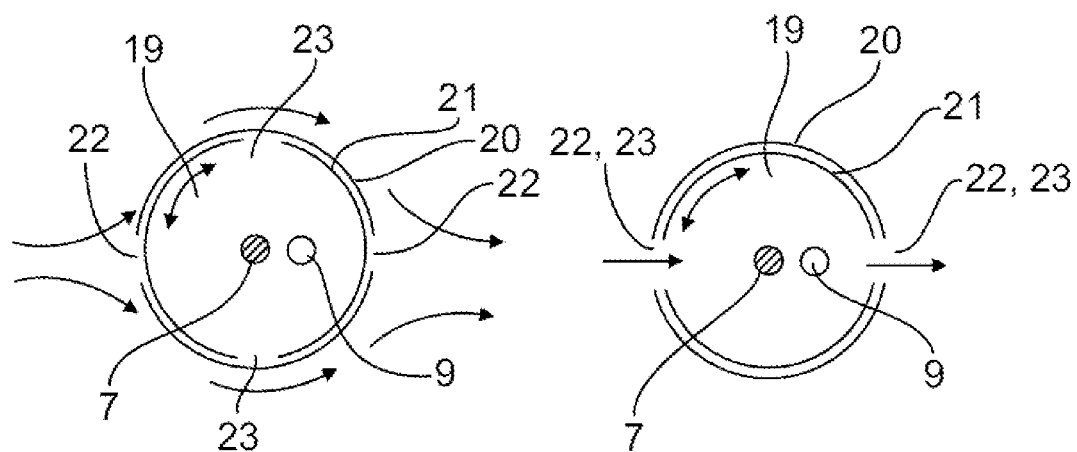
FIG. 4 is a section view along section line A-A in the region of the measurement chamber in FIG. 3 which is formed by two cylinders arranged one inside the other.
FIG. 5 is a section view along section line A-A as in FIG. 4, but with an inner cylinder rotated through 90°.

In the exemplary embodiment shown, the outer cylinder 20 and the inner cylinder 21 each have bores 22, 23 arranged offset by 180° (FIG. 4). In FIG. 3 these bores 22, 23—as in the section view in FIG. 4—are arranged non-aligned so that the measurement chamber 19 is blocked to the exhaust gas flow. The inner cylinder 21 can however be rotated by 90°, according to the double arrow shown, into a position shown in FIG. 5. In this position the bores 22, 23 align so that a part of the exhaust gas can flow into and through the measurement chamber 19. In the position shown in FIG. 5, the measurement chamber 19 is open to the exhaust gas flow so that the exhaust gas sensor 7 can perform an exhaust gas measurement for the oxygen proportion or $NO_x$ concentration. If however the inner cylinder 21 is in the position shown in FIG. 4, the system is in a calibration phase in which calibration gas can be introduced into the measurement chamber 19 via the gas pipe 9.

A further suction line (not shown here) can be connected to the measurement chamber 19 in order to be able to introduce gas via the gas pipe 9 unhindered when the measurement chamber 19 is closed. The cylinders 20, 21 can however also have gas-permeable regions to allow the accelerated introduction of gas.

The invention claimed is:

1. A method for calibrating an exhaust gas sensor, wherein the exhaust gas sensor is arranged in a measurement chamber in an exhaust channel of an internal combustion engine, the measurement chamber including two perforated cylinders arranged concentrically one inside the other, at least one of the two perforated cylinders being movable about a longitudinal axis thereof so that the two cylinders form a screening device with a variable screening effect, the two perforated cylinders each have at least two bores in cylinder walls of the two perforated cylinders, wherein the two perforated cylinders are movable from a non-aligned position into an aligned position to open the measurement chamber to inflowing exhaust gas, the method comprising:
displacing, at a start of a calibration phase, exhaust gas present in the measurement chamber by filling the measurement chamber with a calibration gas; and
introducing exhaust gas into the measurement chamber at an end of the calibration phase by moving the two perforated cylinders into the aligned position.

2. The method according to claim 1, wherein the step of filling comprises introducing calibration gas into the measurement chamber throughout the entire calibration phase so that a pressure in the measurement chamber is maintained higher than a pressure predominating in the exhaust channel.

3. The method according to claim 2, wherein during the calibration phase, the measurement chamber is largely screened from the exhaust gas flow in the exhaust channel.

4. The method according to claim 1, further comprising, after the end of the calibration phase, at least one of drawing and pressing the exhaust gas into the measurement chamber.

5. The method according to claim 4, wherein, after the end of the calibration phase, the exhaust gas is drawn into the measurement chamber by a suction device.

6. The method according to claim 4, wherein after the end of the calibration phase, the measurement chamber is connected fluidically to a part of the exhaust system having a higher pressure than a pressure in the measurement chamber, so that the exhaust gas is pressed into the measurement chamber.

7. The method according to claim 1, wherein the internal combustion engine is charged, and compressed fresh air from at least one compressor is used as a calibration gas.

8. A device for calibrating an exhaust gas sensor, comprising:
a measurement chamber in which the exhaust gas sensor is arranged, the measurement chamber being arranged in an exhaust channel of an internal combustion engine, the measurement chamber including two perforated cylinders arranged concentrically one inside the other, at least one of the two perforated cylinders is movable about its longitudinal axis so that the two cylinders form a screening device selectively screening the measurement chamber from an exhaust gas flow in the exhaust channel; and
a gas pipe connected to the measurement chamber for exposing the measurement chamber to a calibration gas.

9. The device according to claim 8, wherein the two perforated cylinders each have at least two bores in cylinder walls of the two perforated cylinders, wherein the two perforated cylinders are movable from a non-aligned position into an aligned position to open the measurement chamber to inflowing exhaust gas.

10. The device according to claim 8, further comprising a controllable suction device connected to the measurement chamber, and configured to draw the exhaust gas into the measurement chamber after the end of the calibration phase.

11. The device according to claim 10, wherein the suction device comprises a suction line and a controllable valve.

12. The device according to claim 8, wherein the measurement chamber is connected fluidically to a part of an exhaust flow from the internal combustion engine having a higher pressure than a pressure in the measurement chamber, whereby the exhaust gas in the exhaust flow is pressed into the measurement chamber.

13. The device according to claim 12, wherein the part of the exhaust flow having a higher pressure than a pressure in the measurement chamber is upstream of an exhaust turbine of an exhaust gas turbocharger so that the exhaust gas is extracted from the exhaust flow upstream of the exhaust gas turbine of the exhaust turbocharger.

14. The device according to claim 8, wherein the sensor is one of a lambda sensor and an $NO_x$ sensor.

15. The device according to claim 8, wherein the cylinders include gas permeable regions allowing accelerated introduction of gas via the gas pipe.

16. A vehicle with a device according to claim 8.

* * * * *